United States Patent [19]

Williams et al.

[11] Patent Number: 5,395,994
[45] Date of Patent: Mar. 7, 1995

[54] METHOD FOR RECOVERING METHANOL SOLVENT

[75] Inventors: Robert E. Williams; William J. Cranston, III, both of Magnolia, Ark.

[73] Assignee: Albemarle Corporation, Richmond, Va.

[21] Appl. No.: 245,949

[22] Filed: May 19, 1994

Related U.S. Application Data

[63] Continuation of Ser. No. 121,578, Sep. 16, 1993, abandoned.

[51] Int. Cl.⁶ .................. C07C 27/26; C07C 29/74; C07C 37/68
[52] U.S. Cl. ..................... 568/913; 568/724; 568/725; 568/726; 568/755; 568/840; 568/888
[58] Field of Search ............. 568/724, 726, 725, 755, 568/749, 810, 812, 840, 888

[56] References Cited

U.S. PATENT DOCUMENTS

| | | |
|---|---|---|
| 3,029,291 | 4/1962 | Dietzler . |
| 3,182,088 | 5/1965 | Hennis . |
| 3,234,289 | 2/1966 | Hennis . |
| 3,363,007 | 1/1968 | Majewski et al. . |
| 3,546,302 | 12/1970 | Asadorian et al. . |
| 3,868,423 | 2/1975 | Montanari et al. . |
| 3,929,907 | 12/1976 | Janzon et al. . |
| 4,013,728 | 3/1977 | Brackenridge . |
| 4,036,894 | 7/1977 | Jenker . |
| 4,075,119 | 2/1978 | Schmidt et al. .............. 252/182 |

FOREIGN PATENT DOCUMENTS

| | | |
|---|---|---|
| 0380363 | 1/1990 | European Pat. Off. . |
| 7420082 | 1/1976 | France . |
| 2005259 | 8/1991 | Germany . |
| 0064410 | 3/1985 | Israel . |
| 0225034 | 12/1983 | Japan . |

*Primary Examiner*—Werren B. Lone
*Attorney, Agent, or Firm*—E. E. Spielman, Jr.

[57] ABSTRACT

This invention provides an environmentally acceptable method for recovery of phenolic and brominated phenolic compounds, alcohol solvent, and bromide values from the a reaction medium liquid mixture formed in the production of a tetrabromobisphenol-A predominant product. The process comprises (a) separating the tetrabromobisphenol-A predominant product and alkyl bromide from the reaction medium thereby forming a liquid mixture containing alcohol, phenolic and brominated phenolic compounds, HBr, and water; (b) treating the liquid mixture with a sufficient amount of alkaline or alkaline earth metal hydroxide so as to form a treated aqueous mixture having a pH in the range of from about 9.5 to about 14.0, and containing $MBr_n$, water, alcohol, and soluble salts of the phenolic and brominated phenolic compounds, wherein M is an alkaline or alkaline earth metal ion, and n is the valence of M; (c) distilling alcohol from the treated aqueous mixture of (b); (d) acidifying the treated aqueous mixture from (c) subsequent to distillation with a sufficient amount of acid to precipitate the phenolic and brominated phenolic compounds therefrom; and (e) separating the precipitated phenolic and brominated phenolic compounds from the acidified aqueous mixture of (d).

12 Claims, No Drawings

METHOD FOR RECOVERING METHANOL SOLVENT

This application is a continuation of application Ser. No. 08/121,578, filed Sep. 16, 1993, abandoned.

BACKGROUND

This invention relates to a process for recovering methanol solvent used in the production of 4,4'-isopropylidenebis(2,6-dibromophenol) better known as tetrabromobisphenol-A, hereinafter referred to as TBBPA.

TBBPA is a well known commercial flame retardant. Products comprised predominantly of TBBPA are useful as flame retardants in many macromolecular formulations. The preparation of TBBPA by brominating bisphenol-A in a solvent is well-known. The bromination agent typically is bromine or a bromine-chloride mixture. The solvent can be an alcohol, aqueous acetic acid, a non-polar solvent or a two-phase water-organic system, but is preferably an aliphatic alcohol, most preferably a lower aliphatic alcohol such as methanol or ethanol. The literature is replete with processes for the manufacture of TBBPA, see, for example, U.S. Pat. Nos. 3,029,291; 3,182,088; 3,234,289; 3,363,007; 3,546,302; 3,868,423; 3,929,907; 4,013,728; 4,036,894; 4,112,242; 4,180,684; 4,431,847; 4,451,675; 4,628,124; 4,701,568; 4,783,556; 4,909,997; 4,990,321; 5,008,469; 5,017,728; 5,059,722; 5,059,726; Japanese Kokai 2 (1990) 196,747; EPO 380,363; and British Patent 949,306 incorporated herein by reference as if fully set forth. Most if not all of the foregoing processes describe the recovery of TBBPA from the reaction medium by adding water to precipitate the product as product crystals. The crystals are filtered, washed on the filter to remove impurities and dried. The filtrate from the filter is collected and treated to recover solvent for reuse. Since the filtrate contains HBr and/or bromides, it is desirable to recover any bromide containing species from the filtrate for their bromine value. Bromides may be formed as a result of neutralization of the filtrate stream which contains HBr resulting from the ar-bromination of bisphenol-A.

If a methanol solvent is used, as exemplified in U.S. Pat. No. 3,128,088, the excess solvent may be recovered from the filtrate stream upon completion of the reaction using a methanol distillation column. Depending on the operating conditions selected for the distillation process, a variety of compounds may be present in the column bottoms. Typically, methanol distillation is carried out under basic conditions using an alkali metal hydroxide such as NaOH at a pH of 10–14. Under basic conditions the components present in the distillation column bottoms include sodium salts of brominated phenolics, residual methanol, sodium bromide, trace amounts of acetone, NaOH, water and the like. While the average composition of the distillation column bottoms is quite variable, a typical composition for a distillation process having a pH above 9.5 is 83.75–95.4 weight percent water, less than 0.2 weight percent methanol, 0.9–5.0 weight percent brominated phenolic compounds, 3.0–15.0 weight percent NaBr and 0.1–1.0 weight percent NaOH.

In U.S. Pat. No. 4,431,847, a process is described which removes polyhalogenated phenolic compounds from the distillation column bottoms streams such as those described above by forming an insoluble solid polymer that is easily removed by filtration or centrifugation. This solid polymer is then disposed of by landfill. Due to the increasing undesirability of the use of landfills for industrial waste streams, there is a need for a more environmentally acceptable and less costly means for recovering phenolic compounds from the filtrate and distillation column bottoms streams produced in the production of tetrabromobisphenol-A.

THE INVENTION

This invention provides an environmentally acceptable method for recovery of phenolic and brominated phenolic compounds, alcohol solvent, and bromide values from the reaction medium filtrate streams formed in the production of a tetrabromobisphenol-A predominant product. The process comprises (a) separating the tetrabromobisphenol-A predominant product and alkyl bromide from the reaction medium thereby forming a liquid mixture comprising alcohol, phenolic and brominated phenolic compounds, HBr, and water; (b) treating the liquid mixture with a sufficient amount of alkaline or alkaline earth metal hydroxide so as to form a treated aqueous mixture having a pH in the range of from about 9.5 to about 14.0, and containing $MBr_n$, water, alcohol, and soluble salts of the phenolic and brominated phenolic compounds, wherein M is an alkaline or alkaline earth metal ion, and n is the valence of M; (c) distilling alcohol from the treated aqueous mixture of (b); (d) acidifying the treated aqueous mixture from (c) subsequent to distillation with a sufficient amount of acid to precipitate the phenolic and brominated phenolic compounds thereof; and (e) separating the precipitated phenolic and brominated phenolic compounds from the acidified aqueous mixture of (d).

In another embodiment, this invention provides an improvement in a process for preparing tetrabromobisphenol-A in a alcohol reaction medium. The improvement comprises (a) distilling alcohol from a liquid mixture having a pH in the range of from about 9.5 to about 14.0 initially containing alcohol, water, $MBr_n$, and soluble salts of phenolic and brominated phenolic compounds, thereby forming a distillation bottoms mixture containing $MBr_n$, water, soluble salts of phenolic and brominated phenolic compounds, and a minor amount of alcohol, wherein M is an alkaline or alkaline earth metal ion and n is the valence of M; (b) adding an amount of acid to the distillation bottoms mixture of step (a) sufficient to precipitate the phenolic and brominated phenolic compounds; and (c) separating the precipitated phenolic and brominated phenolic compounds from the distillation bottoms mixture of step (b).

The improved process of the present invention not only provides a facile economic means for isolating the phenolic and brominated phenolic compounds generated in the production of TBBPA, but also provides a method for the recovery of alcohol and bromide values from the reaction medium mixture for reuse and/or recycle. By "bromide values" is meant any one or more inorganic bromine compounds such as $CaBr_2$, NaBr, NaBrO, $MgBr_2$, KBr, and the like which form during the solvent recovery procedure.

According to well known production techniques, TBBPA is prepared by dissolving bisphenol-A in alcohol, and adding bromine to the bisphenol-A in alcohol reaction mass in an amount sufficient to convert bisphenol-A to TBBPA while at the same time forming alkyl bromide. The preferred alcohols used in preparing TBBPA are typically lower alkanols, more preferably, methanol, ethanol, propanol, isopropanol, butanol, isobutanol, tert-butanol and the like, and most preferably methanol.

During the bromination reaction alkyl bromide forms due to the reaction of HBr and alkanol. As the alkyl bromide is formed it is removed from the reaction mass leaving the TBBPA predominant product in a liquid reaction medium mixture comprising lower brominated homologs of bisphenol-A, phenolic and brominated phenolic impurities, bromine, HBr, and alkanol solvent.

Subsequent to the bromination reaction, water is added to the reaction vessel to precipitate the TBBPA predominant product. The TBBPA predominant product is separated from the reaction medium by filtration, centrifugation, decantation, and the like, (preferably centrifugation). The filtrate or centrifugate which contains alkanol, phenolic and brominated phenolic compounds, and water is then neutralized and the alcohol solvent is recovered by distillation for recycle back to the process. Alternatively, solvent may be distilled from the filtrate or centrifugate which has not been neutralized and which contains more than about 10 weight percent HBr in the filtrate.

In the first embodiment, of the invention, after separating the TBBPA predominant product and alkyl bromide from the reaction medium, a sufficient amount of alkaline or alkaline earth metal hydroxide is added to the reaction medium thus remaining so as to form a basic liquid mixture containing $MBr_n$, water, alkanol, and soluble salts of the phenolic and brominated phenolic compounds wherein M and n are defined as above. Alkaline or alkaline earth metal hydroxides useful in forming the basic liquid mixture include, $Ba(OH)_2$, $Ca(OH)_2$, $LiOH$, $Mg(OH)_2$, $NaOH$, $KOH$, and the like. More preferred are NaOH and KOH, with NaOH being the most preferred. Phenolic and brominated phenolic compounds include biphenyl, bisphenol-A, alkylphenol, mono- and polybrominated phenol, mono-, di-, tri-, and tetrabromobisphenol-A, and the like. The amount of alkaline or alkaline earth metal hydroxide added is preferably that amount sufficient to raise the pH of the reaction medium thus remaining to above 9.5, preferably to a range of from about 11 to about 14. Since the reaction mass will contain varying amounts of HBr from the bromination of bisphenol-A, the amount of alkaline or alkaline earth metal hydroxide required to adjust the pH to a range of from about 10 to about 14 will vary widely.

After adjusting the pH of the reaction medium subsequent to removal of the TBBPA product and alkyl bromide, the liquid mixture thus formed is subjected to distillation to remove and recover alkanol solvent from the aqueous liquid mixture. The alkanol is removed from the distillation column in the column overhead. A distillation column bottoms containing water, $MBr_n$, soluble salts of phenolic and brominated phenolic compounds, and a minor amount of alkanol is removed from the bottom of the distillation column. By "minor amount of alkanol" means that the distillation column bottoms contains from about 100 to about 500 ppm alkanol or less. The bottoms from the distillation column is collected and further processed to separate the phenolic and brominated phenolic compounds from the aqueous phase, and to recover the bromide values. It is believed that the soluble salts of the phenolic compounds include di-alkaline or di-alkaline earth metal salts of bisphenol-A, brominated bisphenol-A, and the alkaline or alkaline earth metal salts of phenols and brominated phenols.

A key feature of this invention is the precipitation of phenolic and brominated phenolic compounds from an acidic distillation column bottoms. Accordingly, when the liquid mixture is basic, an amount of acid is added to the distillation column bottoms subsequent to distillation of the liquid mixture sufficient to precipitate phenolic and brominated phenolic compounds. The acid may be any one or more of the mineral acids such as $H_2SO_4$, HCl, HBr, $HNO_3$ and the like with HCl, and HBr being preferred, and HCl being the most preferred. The amount of acid added should be sufficient to decrease the pH of the column bottoms to less than about 7, preferably less than about 5, and most preferably to a range of from about 1 to about 3. This assures that essentially all of the phenolic and brominated phenolic compounds in the column bottoms have been precipitated as organic phenolic and brominated phenolic compounds. While not desiring to be bound by theory, it is believed that acidification of the distillation column bottoms will convert the alkaline or alkaline earth metal salts to alkaline or alkaline earth metal bromides, chlorides, and/or bromine. Any free bromine thus formed can then be used to further brominate any lower brominated phenol and bisphenol-A species to higher brominated phenol and bisphenol-A species thus further decreasing the solubility of these brominated phenolic compounds in the aqueous, acidic column bottoms. Lower brominated phenol and bisphenol-A species include the mono- and di-brominated species such as mono- and di-bromobisphenol-A and the like. Higher brominated phenol and bisphenol-A species include the tri- and tetra-brominated species such as tri- and tetra-bromobisphenol-A and the like.

To assure that further bromination of the lower brominated phenol and bisphenol-A species takes place, chlorine can be added to the aqueous, acidified column bottoms containing bromides to oxidize the bromides to bromine. Chlorine addition to the column bottoms is adjusted by measuring the oxidation reduction potential of the column bottoms with an ORP meter during the chlorine addition. Oxidation-reduction potentials in the range of from about 300 to about 700 mV are generally sufficient to convert bromides to bromine and further brominate any lower brominated phenol and bisphenol-A species.

Once the precipitate has formed, the phenolic and brominated phenolic compounds may be separated from the column bottoms containing the bromides and/or chlorides and water by decantation, coalescing, and the like. The resulting column bottoms containing the bromides and/or chlorides typically contains less than about 0.2 weight percent organics, most preferably, in the range of from about 0.01 to about 0.15 weight percent organics.

In general, the process is conducted under atmospheric pressures since this is most economical. However, pressure is not critical to the process of this invention, thus pressures ranging from subatmospheric to superatmospheric may also be used.

Likewise, after distilling the alcohol from the liquid mixture, the subsequent steps of the process may be conducted at any suitable temperature, provided the temperature is below the boiling point of the aqueous column bottoms and not so low that the aqueous phase or organic phase thus formed freezes. Suitable temperatures for the purpose of this invention range from 25° to about 105° C.

In another embodiment of the invention, the step of adjusting the pH of the reaction medium subsequent to the removal of the TBBPA product and alkyl bromide to above 9.5 is omitted. In this case, the HBr content of the liquid mixture thus formed is adjusted to greater than about 10 weight percent HBr prior to distillation to recover the alcohol solvent. The HBr content of the liquid mixture can be adjusted to greater than 10 weight percent by removing water or by the addition of a sufficient amount of HBr to the liquid mixture. Since the pH remains below 7 in the HBr adjusted liquid mixture, very little of the phenolic and brominated phenolic compounds remain dissolved in the aqueous phase once the alkanol is distilled from the acidified liquid mixture. Accordingly, these phenolic compounds can readily be removed from the bottom of the alkanol distillation column as a precipitate without the need to add additional acid to the column bottoms.

Regardless of whether or not an aqueous inorganic base is added to the remaining reaction medium to adjust the pH to above 9.5 prior to the distillation step, an aqueous phase containing bromides may be collected and recycled for recovery of bromide values. If the remaining reaction medium is acidic prior to distillation, phenolic and brominated phenolic compounds will form precipitate in the distillation column bottoms which can readily be isolated from the bromides. If the pH of the remaining reaction medium is adjusted to above 9.5 before distillation, then acidification of the distillation column bottoms is desirable to isolate the phenolic and brominated phenolic compounds from the aqueous phase containing bromides.

The following examples illustrate features of this invention.

EXAMPLE 1

In a reaction vessel was placed 1000 parts methanol and 230 parts of bisphenol-A. Bromine was fed over a 90 minute period in an amount between 0.99 and 0.995 times the theoretical amount needed to covert the bisphenol-A to tetrabromobisphenol-A. The method for brominating the bisphenol-A was generally in accordance with the method disclosed in U.S. Pat. No. 4,783,556, incorporated herein by references as is fully set forth. The reaction mixture was held at reflux during the bisphenol-A bromination sequence and methyl bromide was produced during the entire bisphenol-A bromination process. After the bromine addition was completed, the system was held at reflux for 30 minutes to produce additional methyl bromide which was distilled out of the reaction mixture. Heating was stopped and 400 parts of water was added over a 30 minute period to precipitate the TBBPA and to halt methyl bromide production. The reaction medium was then allowed to cool to 30°–40° C. and TBBPA product was removed by centrifugation and wash with 5 parts of methanol and 5 parts of water. The centrate was neutralized with NaOH to a pH of 12–13 and then distilled to remove methanol. The resulting 870 parts of distillation column bottoms contained 1.7 weight percent sodium salts of tetrabromobisphenol-A, 1.7 weight percent sodium salts of tribromobisphenol-A, 0.2 weight percent sodium salts of tribromophenol, 0.2 weight percent sodium salts of other brominated phenolics, 0.5 weight percent NaOH, 0.3 parts of methanol, and about 12 weight percent NaBr.

EXAMPLE 2

To 870 parts of distillation column bottoms formed generally in accordance with the procedure of Example 1, is added HCl to adjust the pH to 1–3. The acidified aqueous column bottoms is phase separated and 30 parts of precipitate containing 46.9 weight percent tribromobisphenol-A, 47.8 weight percent tetrabromobisphenol-A, 5.0 weight percent tribromophenol, and 0.3 weight percent other brominated phenolics is collected. The remaining acidified aqueous column bottoms after separating out the precipitated organics contains, 1.0 part of organics.

EXAMPLE 3

To 870 parts of acidified distillation column bottoms formed generally in accordance with the procedure of Example 2, is added gaseous chlorine to adjust the oxidation-reduction potential to 300–700 mV. Chlorine oxidizes the bromides to bromine which can further brominate the lower brominated phenolics in the column bottoms. The chlorinated aqueous column bottoms is then phase separated and 0.8 parts of precipitate consisting mostly of tribromophenol but containing 1 to 5 weight percent of tetrabromobisphenol-A, 1 to 5 weight percent tribromobisphenol-A, and 1 to 5 weight percent other brominated phenolics is collected. The remaining aqueous column bottoms after separating out the precipitated organics contains 0.6 parts of organics.

Other variations are possible within the spirit and scope of the appended claims.

What is claimed is:

1. A process for recovering phenolic and brominated phenolic compounds, alcohol solvent, and bromide values from reaction medium liquid mixture formed during the production of a tetrabromobisphenol-A predominant product, the process comprising:
   (a) separating the tetrabromobisphenol-A predominant product and alkyl bromide from the reaction medium thereby forming a liquid mixture containing alcohol, phenolic and brominated phenolic compounds, HBr, and water;
   (b) treating the liquid mixture with a sufficient amount of alkaline or alkaline earth metal hydroxide so as to form a treated aqueous mixture having a pH in the range of from about 9.5 to about 14.0, and containing $MBr_n$, water, alcohol, and soluble salts of the phenolic and brominated phenolic compounds, wherein M is an alkaline or alkaline earth metal ion and n is the valence of M;
   (c) distilling alcohol from the treated aqueous mixture of (b);
   (d) acidifying the treated aqueous mixture subsequent to distillation with a sufficient amount of acid to precipitate the phenolic and brominated phenolic compounds therefrom; and
   (e) separating the precipitated phenolic and brominated phenolic compounds from the acidified aqueous mixture of (d).

2. The process of claim 1 wherein the acid is selected from the group consisting of hydrochloric acid and hydrobromic acid.

3. The process of claim 1 wherein the amount of acid is sufficient to form an acidified aqueous mixture having a pH of less than about 5.

4. The process of claim 1 wherein the alkaline or alkaline earth metal hydroxide is NaOH and the amount of NaOH is sufficient to form a treated aqueous mixture having a pH of from about 10 to about 12.

5. The process of claim 1 further comprising feeding an amount of chlorine to the acidified mixture of step (d) in order to oxidize bromide to bromine for further bromination of the phenolic and brominated phenolic compounds therein.

6. The process of claim 1 wherein the alkanol is methanol.

7. An improvement in a process for preparing tetrabromobisphenol-A in an alcohol reaction medium, the improvement comprising
   (a) distilling alcohol from a liquid mixture having a pH in the range of from about 9.5 to about 14.0 initially containing alcohol, water, $MBr_n$, and soluble salts of phenolic and brominated phenolic compounds, thereby forming distillation bottoms mixture containing $MBr_n$, water, soluble salts of phenolic and brominated phenolic compounds, and a minor amount of alcohol, wherein M is an alkaline or alkaline earth metal ion and n is the valence of M;
   (b) adding an amount of acid to the distillation bottoms mixture of step (a) sufficient to precipitate the phenolic and brominated phenolic compounds; and
   (c) separating the precipitated phenolic and brominated phenolic compounds from the acidified distillation bottoms mixture of step (b).

8. The improvement of claim 7 wherein the acid is selected from the group consisting of hydrochloric acid and hydrobromic acid.

9. The improvement of claim 8 wherein the amount of acid is sufficient to form an acidified distillation bottoms mixture having a pH of less than about 5.

10. The improvement of claim 9, wherein the alcohol is methanol.

11. A process for recovering methanol solvent and bromide values from the production of a tetrabromobisphenol-A predominant product made by brominating bisphenol-A in a methanol reaction medium, the process comprising:
   a) separating the tetrabromobisphenol-A predominant product from the reaction medium by precipitation with water and filtration thereby forming a liquid mixture wherein the liquid mixture comprises an organic phase containing methanol and phenolic and brominated phenolic compounds, and an aqueous phase containing HBr, and water;
   b) adjusting the HBr content of the liquid mixture to greater than 10 weight percent HBr so as to form an acidified liquid mixture containing HBr, water, methanol, and a precipitate containing phenolic and brominated phenolic compounds;
   c) distilling methanol from the acidified liquid mixture; and
   d) separating the precipitated phenolic and brominated phenolic compounds from the acidified liquid mixture of step (c).

12. The process of claim 11 further comprising isolating the separated phenolic and brominated phenolic compounds from said acidified liquid mixture.

* * * * *